(12) United States Patent
Hood et al.

(10) Patent No.: US 6,440,103 B1
(45) Date of Patent: Aug. 27, 2002

(54) METHOD AND APPARATUS FOR THERMAL EMULSIFICATION

(75) Inventors: Larry L. Hood, Laguna Hills; Rex E. Doherty, Tustin; William T. Hood, Anaheim, all of CA (US)

(73) Assignee: Surgijet, Inc., Irvine, CA (US)

(*) Notice: Subject to any disclaimer, the term of this patent is extended or adjusted under 35 U.S.C. 154(b) by 0 days.

(21) Appl. No.: 09/271,641

(22) Filed: Mar. 17, 1999

(51) Int. Cl.$^7$ .................................................. A61F 7/12
(52) U.S. Cl. ......................... 604/113; 604/114; 604/43; 606/107
(58) Field of Search .................... 604/113–114, 43; 607/105, 107, 101, 104; 606/27–31, 41, 107; 128/201.13, 204.17

(56) References Cited

U.S. PATENT DOCUMENTS

| | | | |
|---|---|---|---|
| 1,313,861 A | * | 8/1919 | Reid et al. |
| 3,747,598 A | * | 7/1973 | Cowans |
| 4,478,215 A | * | 10/1984 | Hanlon |
| 4,654,024 A | | 3/1987 | Crihenden et al. |
| 4,754,752 A | * | 7/1988 | Ginsburg et al. |
| 5,037,431 A | | 8/1991 | Summers et al. |
| 5,199,951 A | * | 4/1993 | Spears |
| 5,271,087 A | | 12/1993 | Schmid |
| 5,322,504 A | | 6/1994 | Doherty et al. |
| 5,462,521 A | * | 10/1995 | Brucker et al. |
| 5,464,389 A | * | 11/1995 | Stahl |
| 5,562,692 A | | 10/1996 | Bair |
| 5,591,184 A | | 1/1997 | McDonnell et al. |
| 5,616,120 A | | 4/1997 | Andrew et al. |
| 5,620,479 A | * | 4/1997 | Diederich |
| 5,643,299 A | | 7/1997 | Bair |
| 5,653,692 A | * | 8/1997 | Masterson et al. |
| 5,674,226 A | | 10/1997 | Doherty et al. |
| 5,713,864 A | * | 2/1998 | Verkaart |
| 5,735,815 A | | 4/1998 | Bair |
| 5,860,948 A | * | 1/1999 | Buscemi |
| 5,865,790 A | | 2/1999 | Bair |
| 5,999,678 A | * | 12/1999 | Murphy-Chutorian et al. |
| 6,056,745 A | * | 5/2000 | Panescu et al. |
| 6,080,128 A | * | 6/2000 | Sussman et al. |
| 6,156,036 A | | 12/2000 | Sussman et al. |

FOREIGN PATENT DOCUMENTS

| | | |
|---|---|---|
| AU | 096297 | 7/1993 |
| EP | 0 962 205 A1 | 8/1999 |

\* cited by examiner

Primary Examiner—Mark Bockelman
(74) Attorney, Agent, or Firm—Blakely, Sokoloff, Taylor & Zafman LLP

(57) ABSTRACT

A medical device that can emulsify tissue with a heated fluid. The device may include an active heating element that is located within an inner channel at a distal end of a cannula. The cannula is adapted to be inserted into tissue such as a cornea. The active heating element can provide heat to a fluid that flows through the inner channel. The heat can be transferred into a bolus of fluid that is periodically generated by a pump. The heated bolus is then directed onto tissue.

78 Claims, 3 Drawing Sheets

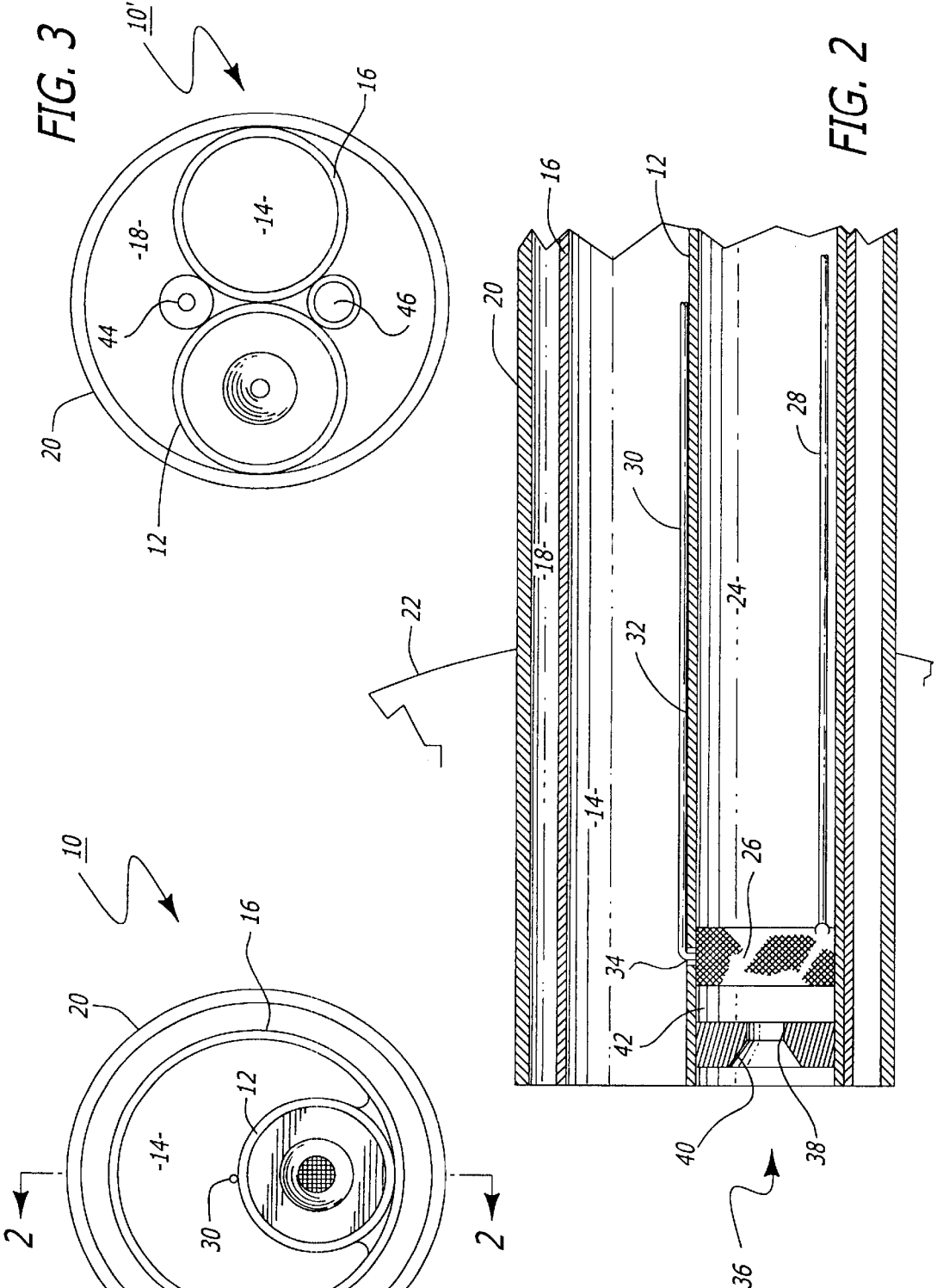

METHOD AND APPARATUS FOR THERMAL EMULSIFICATION

BACKGROUND OF THE INVENTION

1. Field of the Invention

The present invention relates to a medical device that can remove tissue with a bolus of heated fluid.

2. Background Information

There has been developed a medical procedure commonly referred to as phacoemulsification ("phaco") that is performed to remove a cataracteous lens. A phaco procedure typically involves the steps of creating an incision in the cornea and inserting an ultrasonically driven tip that breaks the lens. The tip extends from a handpiece which is held by the surgeon. The handpiece is coupled to an irrigation line and an aspiration system. The irrigation line provides an irrigation fluid to the anterior chamber of the cornea. The aspiration system pulls the irrigation fluid and emulsified lens from the cornea.

Phacoemulsification with an ultrasonic tip typically requires the breaking of the lens into relatively large pieces before emulsification into fragments that can be irrigated. Having to break the lens can be time consuming and may lead to complications in the procedure. It has been found that the lens tissue can be emulsified with a heated liquid. The heated liquid must be introduced into the cornea without burning surrounding corneal tissue such as the epithelium. Burning the epithelium may impair the vision of the patient.

U.S. patent application Ser. No. 08/755,622 U.S. Pat. No. 5,865,790 discloses a device which can emulsify lens tissue with a heated fluid. The device includes a cannula that can be inserted into the cornea. The cannula has an inner channel that is coupled to an irrigation system. A passive heating element is located within the inner channel at a distal end of the cannula. The passive heating element creates heat within the fluid under an isenthalpic process. The generation of heat occurs within the anterior chamber of the cornea at a location away from the epithelium. The heat generated by the passive heating element disclosed in the '622 application is a continuous process. It may be desirable to provide a non-continuous process. For example, it may be desirable to generate a series of heated fluid slugs or a series of heated and non-heated fluid slugs that are directed onto the lens.

The amount of heat generated by the passive element is a function of the pressure drop across the element. The pressure drop is a function of the velocity of the fluid. The heat generated and the corresponding temperature of the irrigation fluid used to emulsify the tissue can be varied by changing the flowrate of the fluid through the cannula. Unfortunately, varying the flowrate must be upstream from the distal end of the cannula. Varying the flowrate upstream introduces a time delay between the change command and the response of the system. It may be desirable to varying the temperature essentially instantaneously. It would therefore desirable to provide a hydro-emulsifier that can generate discrete slugs of heated fluid and can quickly vary the temperature of the heated slugs.

SUMMARY OF THE INVENTION

One embodiment of the present invention includes a medical device that can emulsify tissue with a heated fluid. The device may include an active heating element that is located within an inner channel at a distal end of a cannula. The cannula is adapted to be inserted into tissue such as a cornea. The active heating element can provide heat to a fluid that flows through the inner channel.

BRIEF DESCRIPTION OF THE DRAWINGS

FIG. 1 is an end view of an embodiment of a cannula of the present invention;

FIG. 2 is a cross-sectional view taken at line 2—2 of FIG. 1, showing an active heating element located within an inner channel of the cannula;

FIG. 3 is an end view of an alternate embodiment of the cannula;

DETAILED DESCRIPTION

Figure 4:
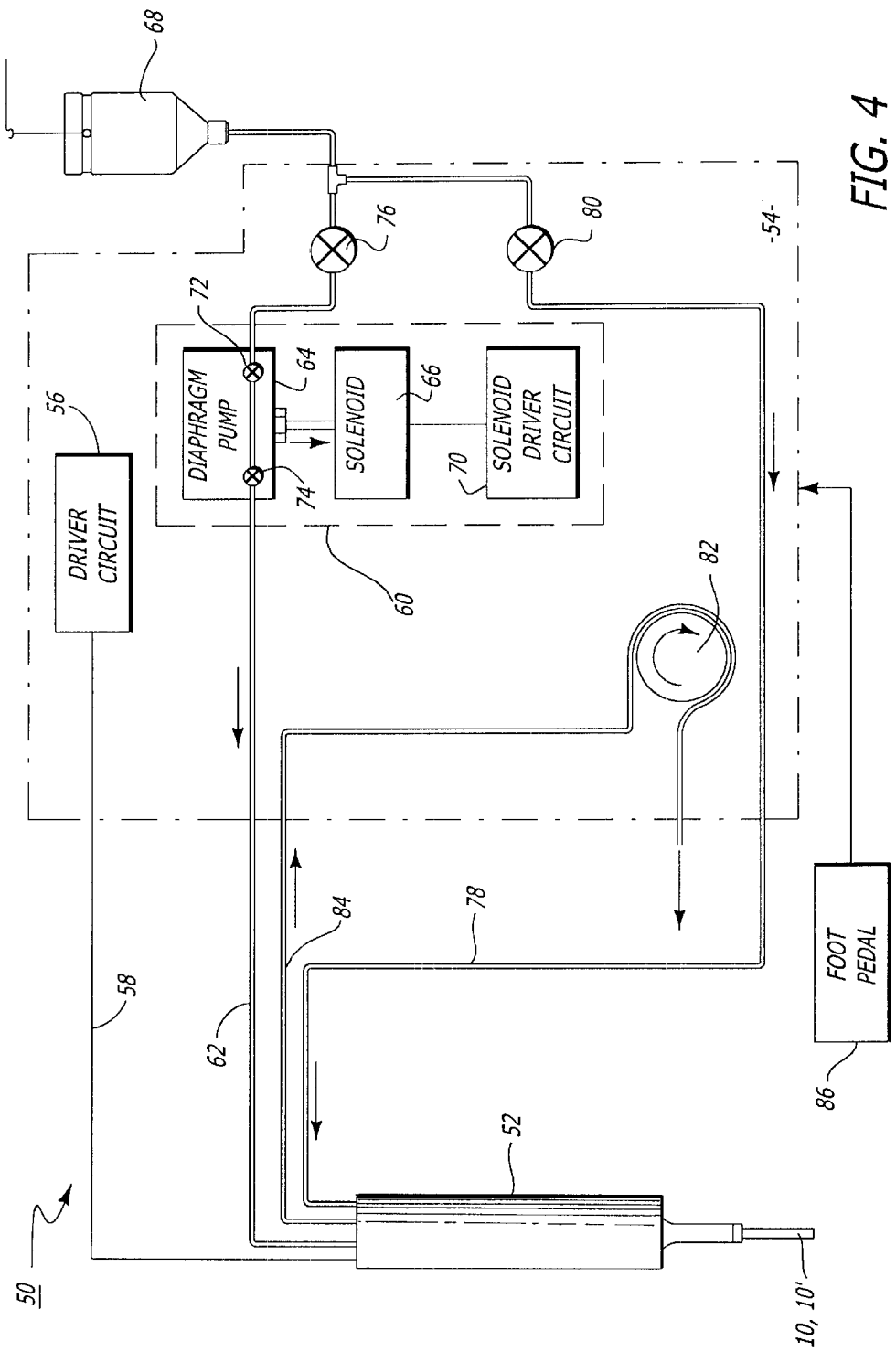
FIG. 4 is a schematic showing a medical system which can deliver fluid and energy to the cannula and active heating element, respectively.

Referring to the drawings more particularly by reference numbers, FIGS. 1 and 2 show a cannula 10 of the present invention. The cannula 10 can deliver heated fluid that may emulsify tissue. For example, the cannula 10 can be inserted into a cornea and the heated fluid may emulsify a cataracteous lens. Although use in an ophthalmic procedure is described, it is to be understood that the cannula 10 can be used to emulsify other tissue. For example, the present invention can be used to emulsify tissue in a "liposuction" procedure.

The cannula 10 may include a first sleeve 12 that is located within an inner channel 14 of a second sleeve 16. The second sleeve 16 may be located within the inner channel 18 of a third sleeve 20. The diameter of the third sleeve 20 may be approximately 1.5 millimeters (mm), small enough to be inserted through an incision in a cornea 22. The sleeves 12, 16 and 20 may be constructed from either a metal or plastic material that will not collapse under the pressure of the cornea at the incision. An irrigation fluid may flow through the inner channel 18 of the third sleeve 20. The irrigation fluid and emulsified tissue may be aspirated through the inner channel 14 of the second sleeve 16.

The irrigation fluid may also flow through an inner channel 24 of the first sleeve 12. An active heating element 26 may be located within the inner channel 24 at the distal end of the sleeve 12. The heating element 26 transfers heat to irrigation fluid that flows through the inner channel 24 to raise the temperature of the fluid. The fluid is typically heated to a temperature that will emulsify tissue. By way of example, the fluid may be heated to a temperature of approximately 180 Fahrenheit (°F).

In one embodiment, the heating element may be an electrically resistive member connected to a current source (not shown) by a pair of wires 28 and 30. One of the wires 28 may extend through the inner channel 24. The other wire 30 may extend along the outer surface 32 of the first sleeve 12 and through an opening 34 to the active heating element 26. Although FIG. 2 shows one type of wire arrangement, it is to be understood that the wires 28 and 30 may be routed in a different manner. For example, both wires 28 and 30 may extend along the outer surface 32 of the first sleeve 12. If the first sleeve 12 is constructed from a metal material the wires 28 and 30 may be coated with an insulative material. If the first sleeve 12 is constructed from a dielectric material such as plastic, the wires 28 and 30 may be plated onto the sleeve 12 with known plating techniques.

The active heating element 26 converts current to thermal heat that is then transferred into the fluid. The heating element 26 may be porous so that the irrigation fluid can flow therethrough, wherein the element 26 functions as a micro-heat exchanger. Locating the heating element 26 at the distal end of the sleeve 12 provides a hydro-emulsifying device that can heat the fluid downstream from the corneal tissue. This reduces the amount of heat that is transferred into the cornea at the point of incision.

By way of example, the heating element 26 may be constructed from a sintered stainless steel UNS number 316. The sintered steel may have a porosity that also filters out particulates in the irrigation fluid. As another embodiment, the heating element 26 may be a non-porous resistive element that is smaller than the diameter of the inner sleeve 26 so that the irrigation fluid can flow past the element 26.

The cannula 10 may have an orifice 36 which has an inlet channel 38 and a tapered outlet 40 that creates a collimated stream of heated irrigation fluid. The orifice 36 can focus the heated fluid onto the tissue that is to be emulsified.

The orifice 36 may be separated from the heating element 26 by a space 42. The space 42 may define a volume or bolus of heated water that is directed onto the tissue by the orifice 36. As an alternate embodiment, the cannula 10 may have a filter at the location of the heating element 26 and a heating element 26 within the space 42 so that the irrigation fluid is filtered and then heated before flowing through the orifice 36.

FIG. 3 shows an alternate embodiment of a cannula 10', wherein the first sleeve 12 and second sleeve 16 are both located within the inner channel 18 of the third sleeve 20. The cannula 10 may further have a fiber optic cable 44 that transmits light to illuminate the surgical site. The cannula 10' may further have a temperature sensor 46 to sense the temperature of the irrigation fluid at the distal end of the sleeves.

FIG. 4 shows an embodiment of a medical system 50. The system 50 includes a handpiece 52 which has a cannula 10 or 10'. The handpiece 52 can be held by a surgeon performing a surgical procedure such as the removal of a cataract. The handpiece 52 is connected to a console 54. The console 54 may contain a driver circuit 56 that is connected to the handpiece 52 by an electrical cable 58. The driver circuit 56 may provide a current to the active heating element 26 shown in FIG. 2. The driver circuit 56 may include a power supply that periodically provides a pulse of power to the active heating element. By way of example, the driver circuit 56 may provide enough electrical power to heat 5–500 micro-liters of irrigation fluid, 100° F., within one second. To accomplish this result the power supply may provide a pulse at 3–6 volts, at a current between 0.5 to 10 amps, for a time duration between 0.1 to 100 milliseconds.

The console 54 may also have a bolus generator 60 that is coupled to the inner channel of the first sleeve by a tube 62. The generator 60 creates a bolus or pulse of fluid that flows into the first sleeve and across the active heating element. The driver circuit 56 may be synchronized with the bolus generator 60 so that power is provided to the active heating element when the bolus of fluid reaches the heating element.

It is preferable to construct the tube 62 from a material that will not significantly expand when subjected to the increase in pressure that results from the creation of the fluid bolus by the generator 60. By way of example, the tube 62 may be constructed from a polyether ether ketone (P.E.E.K.) material wrapped with a KEVLAR material or a metal material.

The bolus generator 60 may include a diaphragm pump 64 that is actuated by a solenoid 66. The pump 64 may be in fluid communication with a reservoir 68 of irrigation fluid. The solenoid 66 may be activated by a solenoid driver circuit 70. The driver circuit 70 may periodically activate and de-active the solenoid 66 which causes a pump chamber within the pump 64 to expand and contract. When the pump chamber expands irrigation fluid flows into the chamber through a one-way valve 72. When the pump chamber contracts the irrigation fluid flows out of the chamber through a one-way valve 74 and into the cannula 10 or 10'. The flow of fluid from the reservoir 68 to the pump 64 may be controlled by a pinch valve 76. Although a solenoid is shown and described, it is to be understood that the pump 64 may be driven by other means such as a piezoelectric or magneto-strictive transducer(s).

The reservoir 68 may also be coupled to the inner channel of the third sleeve by a tube 78 and a pinch valve 80. The inner channel of the second sleeve may be coupled to a peristaltic pump 82 by a tube 84. The pump 82 may pull irrigation fluid and emulsified tissue through the second sleeve. The driver circuit 56, solenoid driver circuit 70 and/or the pump 82 may be coupled to a foot pedal 86 which allows the surgeon to vary the flowrate of fluid and/or the number of fluid pulses per time that are provided to the cannula.

Referring to FIGS. 1, 2 and 4, in operation the surgeon may insert the cannula 10 or 10' through tissue such as a cornea and into a cataracteous lens. Irrigation fluid is allowed to flow through the inner channel 18 of the third sleeve 24. The bolus generator 60 can periodically generate a bolus of fluid that flows into the inner channel 24 of the first sleeve 12. The bolus is heated by the heating element 26 and directed by the orifice 36 into or onto the tissue. The heated bolus of fluid impinges and emulsifies the tissue. The irrigation fluid and emulsified tissue is then aspirated through the inner channel 14 of the second sleeve 16 by the peristaltic pump 82. As one embodiment, the system 50 may create a heated bolus of fluid that is followed by a non-heated bolus of fluid. The series of heated bolus followed by non-heated bolus can be repeated many times.

Figure 5:
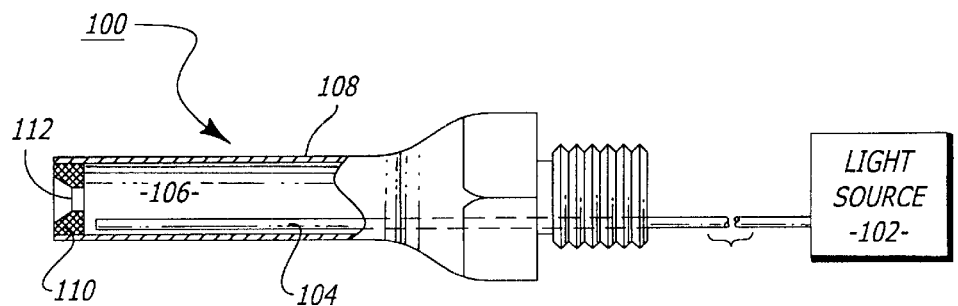
FIG. 5 is a cross-sectional view of an alternate embodiment of a cannula with an optical heating element.

FIG. 5 is an alternate embodiment of a cannula 100 which has an optical heating element. The cannula 100 may include a light source 102 that is coupled to an optical fiber 104 which extends through an inner channel 106 of a first sleeve 108. The light source 102 emits light that is transmitted by the fiber 104 onto an orifice 110. The wavelength of the light, and the material of the orifice 110 are such that the light is absorbed by the orifice material. The absorbed light heats the orifice 110. The heat is transferred to fluid that flows through an opening 112 in the orifice 110. By way of example, the light source 102 may be an xeon flash lamp or a laser.

Figure 6:
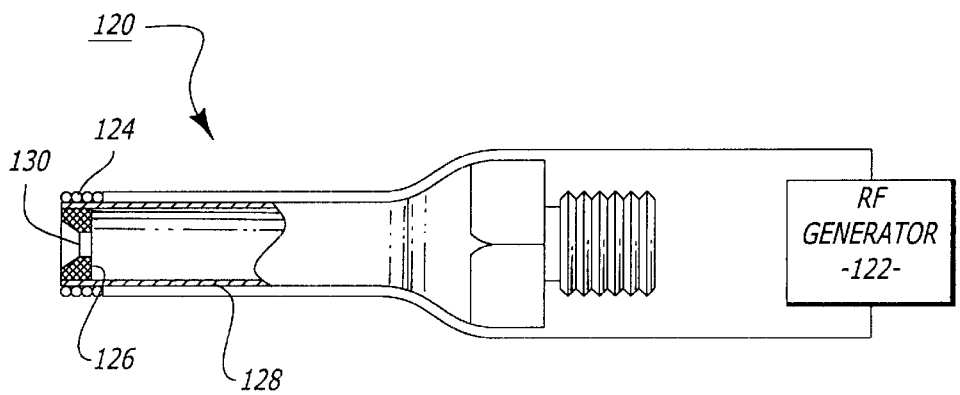
FIG. 6 is a cross-sectional view of an alternate embodiment of a cannula with a radio frequency heating element.

FIG. 6 is an alternate embodiment of a cannula 120 which has a radio frequency heating element. The cannula 120 may include a radio frequency (RF) generator 122 that is connected to a coil 124. The coil 124 is located adjacent to an orifice 126 at the end of a sleeve 128. The generator 122 provides an alternating electrical current to the coil 124 which generates an electric field. The orifice 126 provides a resistance to the electric field wherein there is heat generated in the orifice 126. The heat is transferred into fluid that flows through an opening 130 in the orifice 126.

Figure 7:
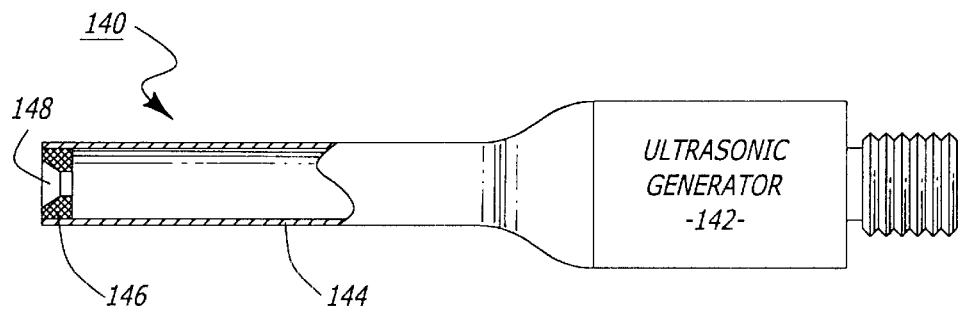
FIG. 7 is a cross-sectional view of an alternate embodiment of a cannula with an ultrasonic heating element.

FIG. 7 is an alternate embodiment of a cannula 140 which has an ultrasonic heating element. The cannula 140 includes an ultrasonic generator 142 that is coupled to a sleeve 144.

The generator 142 can ultrasonically drive the sleeve 144. The cannula 140 may have an orifice 146 that creates an acoustic impedance which results in the generation of heat in the orifice 146. The heat is transferred into fluid that flows through an opening 148 in the orifice 146. The ultrasonic movement of the sleeve 144 may also assist in emulsifying tissue.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A medical device that can be inserted into a tissue, comprising:
    a first sleeve that has a first inner channel that can receive a liquid at a proximal end and discharge the liquid at a distal end, said distal end of the first sleeve extending to a distal end of the medical device;
    a second sleeve which has a second inner channel, wherein said first sleeve is located within said second inner channel;
    a third sleeve that is adapted to be inserted into the tissue and which has a third inner channel, wherein said second sleeve is located within said third inner channel; and
    an active heating element adjacent said first sleeve at said distal end of said first sleeve to heat a bolus of the liquid immediately prior to discharge from said distal end of said first sleeve.

2. The medical device of claim 1, wherein said active heating element includes an electrically resistive member.

3. The medical device of claim 2, wherein said active heating element is porous.

4. The medical device of claim 1, further comprising an orifice located within said first inner channel.

5. The medical device of claim 4, wherein said orifice is separated from said active heating element by a space.

6. The medical device of claim 1, wherein said bolus has a volume between 5 and 500 micro-liters.

7. The medical device of claim 1, further comprising an optical fiber which extends through said first inner channel, wherein said active heating element absorbs light that is transmitted by said optical fiber to heat said active heating element.

8. The medical device of claim 1, further comprising a coil located adjacent to said active heating element, wherein said active heating element provides a resistance to a radio frequency current in said coil to heat said active heating element.

9. The medical device of claim 1, further comprising an ultrasonic generator coupled to said first sleeve, wherein said active heating element creates an acoustic impedance which results in the generation of heat in said active heating element.

10. The medical device of claim 1, wherein said active heater can heat the fluid in said bolus 100° F. within one second.

11. A medical system, comprising:
    a handpiece which has a cannula, said cannula having
        a first sleeve which has a first inner channel that can receive a liquid at a proximal end and discharge the liquid at a distal end, said distal end of the first sleeve extending to a distal end of the handpiece and an active heating element adjacent said first sleeve at said distal end of said first sleeve to heat a bolus of the liquid immediately prior to discharge from said distal end of said first sleeve, and
        a second sleeve which has a second inner channel, wherein said first sleeve is located within said second inner channel;
    a fluid subsystem connected to said proximal end of said first sleeve to provide the liquid to said first inner channel; and,
    a drive circuit that provides a current to said active heating element.

12. The medical system of claim 11, further comprising an orifice located within said first inner channel.

13. The medical system of claim 12, wherein said orifice is separated from said active heating element by a space.

14. The medical device of claim 11, further comprising a third sleeve which has a third inner channel, wherein said second sleeve is located within said third inner channel.

15. The medical system of claim 14, further comprising an irrigation subassembly that is coupled to said third inner channel.

16. The medical system of claim 11, wherein said fluid subsystem includes a bolus generator which generates the bolus of the liquid that flows across said active heating element, wherein said drive circuit provides a current to said active heating element so that heat is generated in said active heating element and transferred to the bolus of the liquid.

17. The medical system of claim 16, further comprising a control device that is coupled to said bolus generator and said drive circuit.

18. The medical system of claim 17, wherein said control device includes a foot pedal.

19. The medical system of claim 11, further comprising an aspiration subassembly that is coupled to said second inner channel.

20. The medical system of claim 11, wherein said active heating element is porous.

21. A method for emulsifying tissue, comprising:
    placing a first sleeve adjacent to the tissue, said first sleeve having a first inner channel;
    flowing a fluid through a second sleeve located within said first inner channel, said second sleeve having a second inner channel; and,
    generating heat within an active heating element located within said second inner channel so that heat is transferred into the fluid at a distal end of the second sleeve, wherein the heated fluid emulsifies tissue.

22. The method of claim 21, further comprising the step of irrigating the heated fluid and emulsified tissue.

23. The method of claim 21, further comprising the step of generating a bolus of fluid that flows through the first sleeve.

24. A medical device that can be inserted into a tissue, comprising:
    a first sleeve that is adapted to be inserted into the tissue and which has an inner channel that can receive a fluid;
    an optical fiber which extends through said inner channel; and,
    an active heating element that is located within said inner channel and can heat the fluid, wherein said active heating element is porous, wherein said active heating element absorbs light that is transmitted by said optical fiber to heat said active heating element.

25. The medical device of claim 24, further comprising an orifice located within said inner channel.

26. The medical device of claim 25, wherein said orifice is separated from said active heating element by a space.

27. The medical device of claim 24, further comprising a second sleeve which has an inner channel, wherein said first sleeve is located within said inner channel of said second sleeve.

28. The medical device of claim 27, further comprising a third sleeve which has an inner channel, wherein said second sleeve is located within said inner channel of said third sleeve.

29. A medical device that can be inserted into a tissue, comprising:
   a first sleeve that has a first inner channel that can receive a liquid at a proximal end and discharge the liquid at a distal end, said distal end of the first sleeve extending to a distal end of the medical device;
   a second sleeve that is adapted to be inserted into the tissue and which has a second inner channel, wherein said first sleeve is located within said second inner channel;
   an optical fiber which extends through said first inner channel; and,
   an active heating element adjacent said first sleeve at said distal end of said first sleeve to heat a bolus of the liquid immediately prior to discharge from said distal end of said first sleeve, wherein said active heating element absorbs light that is transmitted by said optical fiber to heat said active heating element.

30. The medical device of claim 29, further comprising an orifice located within said first inner channel.

31. The medical device of claim 30, wherein said orifice is separated from said active heating element by a space.

32. The medical device of claim 29, wherein said active heating element is porous.

33. A medical device that can be inserted into a tissue, comprising:
   a first sleeve that has a first inner channel that can receive a liquid at a proximal end and discharge the liquid at a distal end, said distal end of the first sleeve extending to a distal end of the medical a device;
   a second sleeve that is adapted to be inserted into the tissue and which has a second inner channel, wherein said first sleeve is located within said second inner channel;
   an active heating element adjacent said first sleeve at said distal end of said first sleeve to heat a bolus of the liquid immediately prior to discharge from said distal end of said first sleeve; and,
   a coil located adjacent to said active heating element, wherein said active heating element provides a resistance to a radio frequency current in said coil to heat said active heating element.

34. The medical device of claim 33, further comprising an orifice located within said first inner channel.

35. The medical device of claim 34, wherein said orifice is separated from said active heating element by a space.

36. The medical device of claim 33, wherein said active heating element is porous.

37. A medical device that can be inserted into a tissue, comprising:
   a first sleeve that has a first inner channel that can receive a liquid at a proximal end and discharge the liquid at a distal end, said distal end of the first sleeve extending to a distal end of the medical device;
   a second sleeve that is adapted to be inserted into the tissue and which has a second inner channel, wherein said first sleeve is located within said second inner channel; and
   an active heating element adjacent said first sleeve at said distal end of said first sleeve to heat a bolus of the liquid immediately prior to discharge from said distal end of said first sleeve, wherein said active heating element is porous.

38. The medical device of claim 37, further comprising an orifice located within said first inner channel.

39. The medical device of claim 38, wherein said orifice is separated from said active heating element by a space.

40. The medical device of claim 37, wherein said active heating element includes an electrically resistive member.

41. The medical device of claim 37, further comprising an optical fiber which extends through said first inner channel, wherein said active heating element absorbs light that is transmitted by said optical fiber to heat said active heating element.

42. The medical device of claim 37, further comprising a coil located adjacent to said active heating element, wherein said active heating element provides a resistance to a radio frequency current in said coil to heat said active heating element.

43. The medical device of claim 37, further comprising an ultrasonic generator coupled to said first sleeve, wherein said active heating element creates an acoustic impedance which results in the generation of heat in said active heating element.

44. A medical system, comprising:
   a handpiece which has a cannula, said cannula having
      a first sleeve which has a first inner channel that can receive a liquid at a proximal end and discharge the liquid at a distal end, said distal end of the first sleeve extending to a distal end of the handpiece and an active heating element adjacent said first sleeve at said distal end of said first sleeve to heat a bolus of the liquid immediately prior to discharge from said distal end of said first sleeve,
      a second sleeve which has a second inner channel, wherein said first sleeve is located within said second inner channel, and
      a third sleeve which has a third inner channel, wherein said second sleeve is located within said third inner channel;
   a fluid subsystem that provides the liquid to said first inner channel; and,
   a drive circuit that provides a current to said active heating element.

45. The medical system of claim 44, further comprising an orifice located within said first inner channel.

46. The medical system of claim 45, wherein said orifice is separated from said active heating element by a space.

47. The medical system of claim 44, wherein said fluid subsystem includes a bolus generator which generates the bolus of the liquid that flows across said active heating element, wherein said drive circuit provides a current to said active heating element so that heat is generated in said active heating element and transferred to the bolus of the liquid.

48. The medical system of claim 47, further comprising a control device that is coupled to said bolus generator and said drive circuit.

49. The medical system of claim 48, wherein said control device includes a foot pedal.

50. The medical system of claim 44, further comprising an irrigation subassembly that is coupled to said third inner channel.

51. The medical system of claim 44, further comprising an aspiration subassembly that is coupled to said second inner channel.

52. The medical system of claim 44, wherein said active heating element is porous.

53. A medical system, comprising:
a handpiece which has a cannula, said cannula having
a first sleeve which has a first inner channel that can receive a liquid at a proximal end and discharge the liquid at a distal end, said distal end of the first sleeve extending to a distal end of the handpiece and an active heating element adjacent said first sleeve at said distal end of said first sleeve to heat a bolus of the liquid immediately prior to discharge from said distal end of said first sleeve, and
a second sleeve which has a second inner channel, wherein said first sleeve is located within said second inner channel;
a fluid subsystem that provides the liquid to said first inner channel, said fluid subsystem including a bolus generator which generates the bolus of the liquid that flows across said active heating element, wherein said drive circuit provides a current to said active heating element so that heat is generated in said active heating element and transferred to the bolus of the liquid;
a drive circuit that provides a current to said active heating element; and
a control device that is coupled to said bolus generator and said drive circuit, said control device including a foot pedal.

54. The medical system of claim 53, further comprising an orifice located within said first inner channel.

55. The medical system of claim 54, wherein said orifice is separated from said active heating element by a space.

56. The medical device of claim 53, further comprising a third sleeve which has a third inner channel, wherein said second sleeve is located within said third inner channel.

57. The medical system of claim 56, further comprising an irrigation subassembly that is coupled to said third inner channel.

58. The medical system of claim 53, further comprising an aspiration subassembly that is coupled to said second inner channel.

59. The medical system of claim 53, wherein said active heating element is porous.

60. A medical system, comprising:
a handpiece which has a cannula, said cannula having
a first sleeve which has a first inner channel that can receive a liquid at a proximal end and discharge the liquid at a distal end, said distal end of the first sleeve extending to a distal end of the handpiece,
an active heating element adjacent said first sleeve at said distal end of said first sleeve to heat a bolus of the liquid immediately prior to discharge from said distal end of said first sleeve, said active heating element being porous, and
a second sleeve which has a second inner channel, wherein said first sleeve is located within said second inner channel;
a fluid subsystem that provides the liquid to said first inner channel; and,
a drive circuit that provides a current to said active heating element.

61. The medical system of claim 60, further comprising an orifice located within said first inner channel.

62. The medical system of claim 61, wherein said orifice is separated from said active heating element by a space.

63. The medical device of claim 60, further comprising a third sleeve which has a third inner channel, wherein said second sleeve is located within said third inner channel.

64. The medical system of claim 63, further comprising an irrigation subassembly that is coupled to said third inner channel.

65. The medical system of claim 60, wherein said fluid subsystem includes a bolus generator which generates the bolus of the liquid that flows across said active heating element, wherein said drive circuit provides a current to said active heating element so that heat is generated in said active heating element and transferred to the bolus of the liquid.

66. The medical system of claim 65, further comprising a control device that is coupled to said bolus generator and said drive circuit.

67. The medical system of claim 66, wherein said control device includes a foot pedal.

68. The medical system of claim 60, further comprising an aspiration subassembly that is coupled to said second inner channel.

69. A medical device that can be inserted into a tissue, comprising:
a first sleeve that is adapted to be inserted into the tissue and which has an inner channel that can receive a fluid;
an orifice located within said inner channel;
an optical fiber which extends through said inner channel; and,
an active heating element that is located within said inner channel and can heat the fluid, wherein said active heating element absorbs light that is transmitted by said optical fiber to heat said active heating element.

70. The medical device of claim 69, wherein said active heating element is porous.

71. The medical device of claim 69, wherein said orifice is separated from said active heating element by a space.

72. The medical device of claim 69, further comprising a second sleeve which has an inner channel, wherein said first sleeve is located within said inner channel of said second sleeve.

73. The medical device of claim 72, further comprising a third sleeve which has an inner channel, wherein said second sleeve is located within said inner channel of said third sleeve.

74. A medical device that can be inserted into a tissue, comprising:
a first sleeve which has an inner channel that can receive a fluid;
a second sleeve that is adapted to be inserted into the tissue and which has an inner channel, wherein said first sleeve is located within said inner channel of said second sleeve;
an optical fiber which extends through said first inner channel; and,
an active heating element that is located within said inner channel of said first sleeve and can heat the fluid, wherein said active heating element absorbs light that is transmitted by said optical fiber to heat said active heating element.

75. The medical device of claim 74, wherein said active heating element is porous.

76. The medical device of claim 74, further comprising an orifice located within said inner channel of said first sleeve.

77. The medical device of claim 76, wherein said orifice is separated from said active heating element by a space.

78. The medical device of claim 74, further comprising a third sleeve which has an inner channel, wherein said second sleeve is located within said inner channel of said third sleeve.

* * * * *